United States Patent [19]

Harrap

[11] Patent Number: 4,892,735
[45] Date of Patent: Jan. 9, 1990

[54] PLATINUM CHEMOTHERAPEUTIC PRODUCT

[75] Inventor: Kenneth R. Harrap, Peaslake, Nr. Guildford, England

[73] Assignee: Johnson Matthey Public Limited Company, London, England

[21] Appl. No.: 324,054

[22] Filed: Mar. 16, 1989

[30] Foreign Application Priority Data

Mar. 16, 1988 [GB] United Kingdom ................. 8806224

[51] Int. Cl.$^4$ .............................................. A61E 9/02
[52] U.S. Cl. .................................... 424/435; 424/422; 424/464; 424/489; 514/867
[58] Field of Search ................ 556/137; 514/397, 492, 514/275, 867, 872; 424/435, 464, 489

[56] References Cited

U.S. PATENT DOCUMENTS

| | | | |
|---|---|---|---|
| 3,714,159 | 1/1973 | Janssen | 544/176 X |
| 4,116,963 | 9/1978 | Adelstein | 514/867 X |
| 4,175,133 | 11/1979 | Gale et al. | 514/492 |
| 4,194,045 | 3/1980 | Adelstein | 514/867 X |
| 4,443,467 | 4/1984 | Ward | 514/275 X |
| 4,536,386 | 8/1985 | Keenan | 424/131 X |
| 4,599,352 | 7/1986 | Narayanan et al. | 514/492 |
| 4,721,720 | 1/1988 | Wootton et al. | 524/304 |
| 4,725,603 | 2/1988 | Sanger et al. | 514/305 |
| 4,753,789 | 6/1988 | Tyers et al. | 514/397 |
| 4,793,986 | 12/1988 | Serino et al. | 514/54 |

Primary Examiner—Thurman K. Page
Attorney, Agent, or Firm—Cushman, Darby & Cushman

[57] ABSTRACT

Certain platinum co-ordination compounds, but not cisplatin, exhibit increased bioavailability when given by the oral route in combination with loperamide.

10 Claims, No Drawings

PLATINUM CHEMOTHERAPEUTIC PRODUCT

This invention relates to platinum chemotherapeutic products for the treatment of cancer.

Certain platinum coordination compounds are known for clinical use in the treatment of various forms of cancer, and are generally analogues of the first compound recognised as exhibiting anti-cancer activity, namely cis-diammine-dichloroplatinum (II), known generically as cisplatin. However, indices of activity and toxicity vary widely from compound to compound and it has for several years been an objective of the researcher to provide a compound with a combination of good activity with low toxicity, particularly since the toxicity generally manifests itself in the form of extreme vomiting and diarrhoea which the patient finds extremely unpleasant and has difficulty in tolerating, leading to a tendency to voluntary rejection of the therapy. However, some success has been achieved and certain compounds show desirable properties, although it remains a goal to improve activity, either in terms of spectrum of activity in absolute terms or against certain specified cancers, while reducing toxicity.

A further objective of the researcher has been to provide a compound which exhibits useful anti-tumour activity following oral administration. It has been found, however, that such activity cannot be predicted on the basis of or by extrapolation from results following intraperitoneal administration and much effort has been expended on pharmacokinetics studies, in an attempt to determine the factors which affect absorption and retention in the systemic circulation following oral administration.

It is an object of the present invention to provide a chemotherapeutic product for the treatment of cancer and which exhibits enhanced activity following oral administration.

According to the invention, a chemotherapeutic product comprises a platinum coordination compound having the general formula

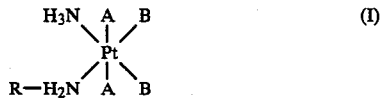

in which R is H, methyl, ethyl or a straight chain, branched chain or cyclic alkyl group having from 3 to 9 carbon atoms, A is a chlorine or hydroxyl group and is present only when the platinum atom is in the Pt (IV) state, and each B is a chlorine atom or together form a malonate or substituted malonate, providing B is not chlorine when R is hydrogen, and loperamide, as a combined preparation for simultaneous, separate or sequential use in the treatment of cancer.

The invention also includes pharmaceutical products containing a platinum coordination compound having the general formula (I) and loperamide. Furthermore, the invention includes pharmaceutical compositions comprising such products together with a pharmaceutically acceptable carrier or diluent. Suitable carriers and diluents are well known, as are the principles of formulation of compositions in unit dosage form and for oral administration.

In a further aspect, the invention includes a method for the treatment of cancer in an animal or human body, the method comprising the simultaneous, separate or sequential administration to the said body of a platinum coordination compound having the general formula (I) and loperamide.

Loperamide (4-p-chlorophenyl)-4-hydroxy-N,N-dimethyl-α,α-diphenyl-1-piperidinebutyramide) is a known antidiarrhoel agent and its preparation and characterisation were first described in French Patent No. 2,100,711, corresponding to U.S. Pat. No. 3,714,159. We have found according to the invention that loperamide significantly increases the absorption of the platinum compound into the systemic circulation following oral administration and causes a marked increase in anti-tumour activity as measured by reduction in tumour size in test animals. Furthermore, we have found that the beneficial effects of loperamide are not shown by combined administration with any platinum compound selected at random from the range of known such compounds exhibiting anti-tumour activity, but rather appear to have a selective effect with certain platinum compounds or classes of platinum compound only. For example, no beneficial effect is apparent from the administration of loperamide and cisplatin, but a marked effect is noted from the administration of loperamide and carboplatin, diammine-1,1-cyclobutanedicarboxylateplatinum (II), which is a platinum (II) compound according to general formula (I) in which R is H and the B's together form 1,1-cyclobutanedicarboxylate.

Other platinum coordination compounds which show a beneficial effect in combination with loperamide include mixed amine compounds with halogen leaving groups ligands, such as cis-dichloro (ammine) (isobutylamine) platinum (II) and platinum (IV) compounds such as cis-diammine-dichloro-trans-dihydroxyplatinum (IV), cis-(ammine)-(cyclopentylamine)-tetrachloroplatinum (IV) and cis-dichloro-(ammine)(t-butylamine)-trans-dihydroxyplatinum (IV).

We have obtained the results as shown in the attached Table 1 for combined administration of loperamide with the indicated platinum compounds, where loperamide at a dosage level of 10 mg/kg was administered to mice simultaneously with administration of the platinum compound at a dosage level of 10 μmole/kg. Results are expressed as average percentage (number of animals per test was 3 or 4) of total platinum metal excreted in the urine over 48 hours following administration, plus/minus standard deviation, where a higher urine concentration is indicative of a higher level of absorption into the bloodstream.

It is seen from Table 1 that all compounds tested, except cisplatin, gave a marked beneficial effect in combination with loperamide, to the extent that absorption was increased to approximately 20–25% of the given dose.

Tests were also carried out in bioavailability of the compound carboplatin (cis-diammine-cyclobutanedicarboxylatoplatinum (II)) following combined administration with loperamide. Bioavailability is a measure of the absorption following oral (p.o.) administration compared with intravenous (i.v.) injection and is expressed as:

$$\frac{\% \text{ dose in urine following p.o}}{\% \text{ dose in urine following i.v.}}$$

Results are given in the attached Table 2, from which it can be seen that loperamide enhances the bioavailability of carboplatin following oral administration by over 100%, compared with administration of the compound alone.

Further tests were carried out to determine anti-tumour effectiveness by assessing the reduction in tumour size 10 days after administration to mice bearing the ADJ/PC6 tumour. Dosage levels were 8 mg/kg for the compound carboplatin and 3 mg/kg for the compound cisplatin, in each case with and without loperamide. Results are given in the attached Table 3, from which it can be seen that the selective effect of loperamide, already noted from Table 1, is reinforced. Results are quoted as average volume reduction over 5 animals per test, plus/minus standard error.

TABLE 1
ABSORPTION STUDIES

| Compound | % Dose in Urine Control | % Dose in Urine + Loperamide |
|---|---|---|
| $\text{NH}_3\text{-Pt(NH}_3\text{)-Cl}_2$ (cisplatin structure) | 21 ± 2 | 18 ± 10 |
| diammine Pt cyclobutanedicarboxylate | 9 ± 2 | 21 ± 5 |
| NH$_3$/c-C$_5$H$_9$NH$_2$ Pt cyclobutanedicarboxylate | 15 ± 3 | 27 ± 7 |
| NH$_3$/i-C$_4$H$_9$NH$_2$ Pt cyclobutanedicarboxylate | 6 ± 4 | 24 ± 10 |
| NH$_3$/i-C$_4$H$_9$NH$_2$ PtCl$_2$ | 7 ± 2 | 19 ± 3 |
| NH$_3$/NH$_3$ Pt(OH)$_2$Cl$_2$ | 15 ± 2 | 23 ± 2 |
| NH$_3$/c-C$_5$H$_9$NH$_2$ PtCl$_4$ | 6 ± 2 | 19 ± 3 |
| NH$_3$/t-C$_4$H$_9$NH$_2$ Pt(OH)$_2$Cl$_2$ | 11 ± 0.2 | 17 ± 5 |

TABLE 2
BIOAVAILABILITY

| DRUG | % DOSE IN URINE 0–48 HR p.o. | % DOSE IN URINE 0–48 HR i.v. | BIOAVAILABILITY |
|---|---|---|---|
| Carboplatin | 11 ± 2 | 66 ± 13 | 16% |
| Carboplatin + loperamide | 25 ± 10 | 72 ± 12 | 34% |

TABLE 3
ANTI-TUMOUR EFFECTIVENESS

| DRUG | % REDUCTION IN TUMOUR SIZE |
|---|---|
| Cisplatin | 88.1 ± 3.5 |
| Cisplatin + loperamide | 81.6 ± 2.6 |
| Carboplatin | 25.9 ± 7.1 |
| Carboplatin + loperamide | 74.3 ± 11.8 |

I claim:

1. A chemotherapeutic product comprising a platinum coordination compound of the general formula I,

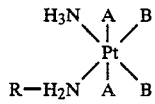

$$\begin{array}{c} H_3N \quad A \quad B \\ \diagdown | \diagup \\ Pt \\ \diagup | \diagdown \\ R-H_2N \quad A \quad B \end{array} \quad (I)$$

wherein R is hydrogen, methyl, ethyl or a straight chain or branched chain or cyclic alkyl group having from 3 to 9 carbon atoms, A is a chlorine atom or hydroxyl group and is present when the platinum atom is in the Pt (IV) state, and each B is a chlorine atom or together form a malonate or substituted malonate, providing B is not chlorine when R is hydrogen, and loperamide, as a combined preparation for simultaneous, separate or sequential use in the treatment of cancer.

2. A product as claimed in claim 1, wherein the platinum compound and the loperamide are each in oral unit dosage form.

3. A product as claimed in claim 1, wherein the platinum compound has B substituents which together form a 1,1-cyclobutanedicarboxylate.

4. A product as claimed in claim 3, wherein the platinum compound is carboplatin.

5. A pharmaceutical composition comprising a platinum compound of formula I defined in claim 1, and loperamide, together with a pharmaceutically acceptable carrier or diluent.

6. A composition as claimed in claim 5, in oral unit dosage form.

7. A composition as claimed in claim 5, wherein the platinum compound has B substituents which together form a 1,1-cyclobutanedicarboxylate.

8. A composition as claimed in claim 7, wherein the platinum compound is carboplatin.

9. A method of treatment of cancer in an animal or human body, the method comprising the simultaneous, separate or sequential administration to the animal or human body of an effective amount of a platinum coordination compound of the general formula I defined in claim 1 and loperamide.

10. The method of claim 9, wherein administration is by the oral route.